(12) United States Patent
Vaillancourt

(10) Patent No.: US 9,044,583 B2
(45) Date of Patent: Jun. 2, 2015

(54) VALVE FOR INTRODUCER NEEDLE

(76) Inventor: Michael J. Vaillancourt, Chester, NJ (US)

( * ) Notice: Subject to any disclaimer, the term of this patent is extended or adjusted under 35 U.S.C. 154(b) by 2342 days.

(21) Appl. No.: 11/134,012

(22) Filed: May 20, 2005

(65) Prior Publication Data

US 2006/0264834 A1    Nov. 23, 2006

(51) Int. Cl.
*A61M 5/178* (2006.01)
*A61M 39/06* (2006.01)
*A61M 25/06* (2006.01)

(52) U.S. Cl.
CPC ........ *A61M 39/0606* (2013.01); *A61M 25/0693* (2013.01); *A61M 2039/0633* (2013.01); *A61M 2039/0646* (2013.01); *A61M 2039/066* (2013.01)

(58) Field of Classification Search
CPC .............. A61M 25/0693; A61M 25/0606; A61M 2039/064; A61M 2039/0633; A61M 25/0618

USPC ................. 604/164.01–170.03, 246–256
See application file for complete search history.

(56) References Cited

U.S. PATENT DOCUMENTS

| 3,585,996 | A | * | 6/1971 | Reynolds et al. | ............. 604/158 |
| 4,682,980 | A | * | 7/1987 | Suzuki | .......................... 604/122 |
| 4,935,010 | A | * | 6/1990 | Cox et al. | ...................... 604/122 |
| 5,053,014 | A | * | 10/1991 | Van Heugten | ........... 604/167.03 |
| 5,290,246 | A | * | 3/1994 | Yamamoto et al. | ...... 604/167.03 |
| 5,820,596 | A | * | 10/1998 | Rosen et al. | .................. 604/108 |

* cited by examiner

*Primary Examiner* — Phillip Gray
(74) *Attorney, Agent, or Firm* — Francis C. Hand; Carella, Byrne et al.

(57) ABSTRACT

A valve is provided for mounting on the hub of an introducer needle to provide a flashback chamber, to prevent outflow of blood from the introducer needle and to allow a guide wire to be inserted into the introducer needle in a bloodless seal-tight manner. The valve employs a seal ring having a slit through which the guide wire may be passed. A port is also provided to vent air from the introducer needle through an air filter that prevents passage of blood.

5 Claims, 2 Drawing Sheets

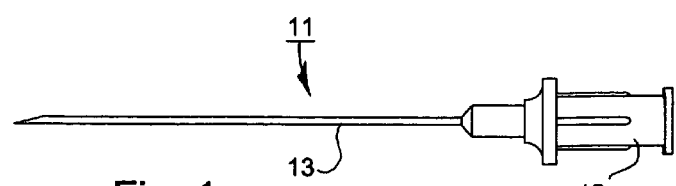
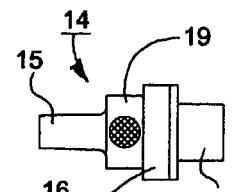
Fig. 1
Fig. 2
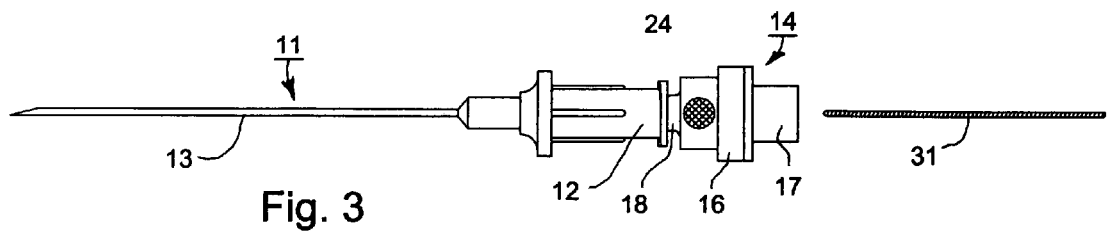
Fig. 3
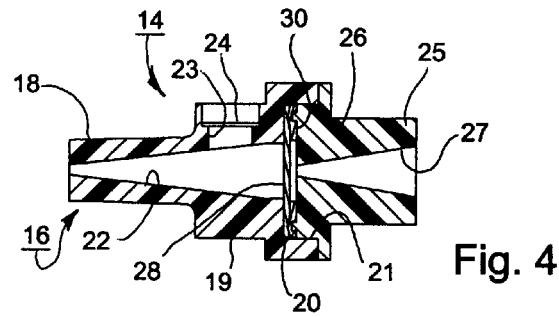
Fig. 4
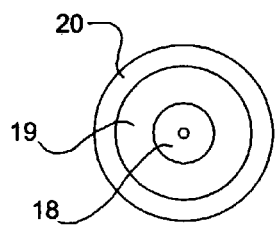
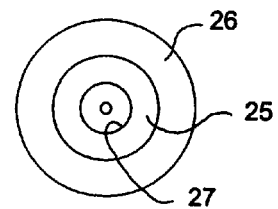
Fig. 5
Fig. 6

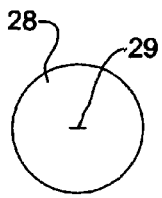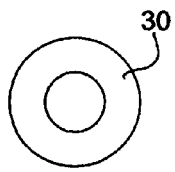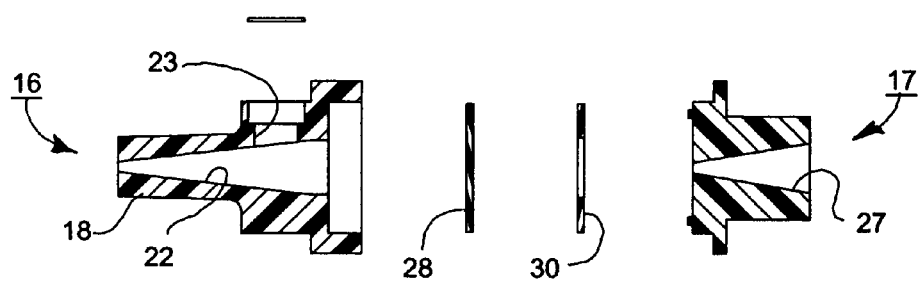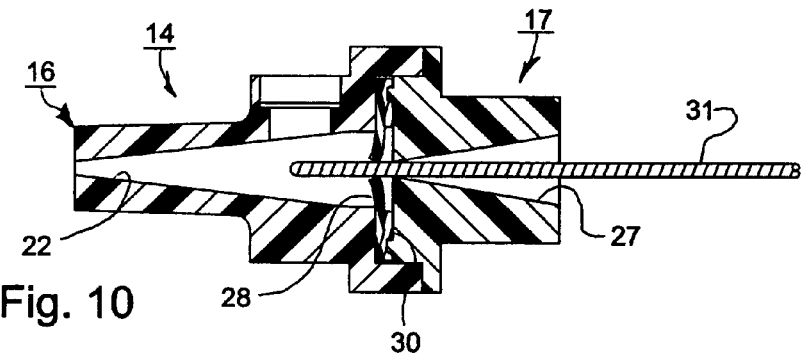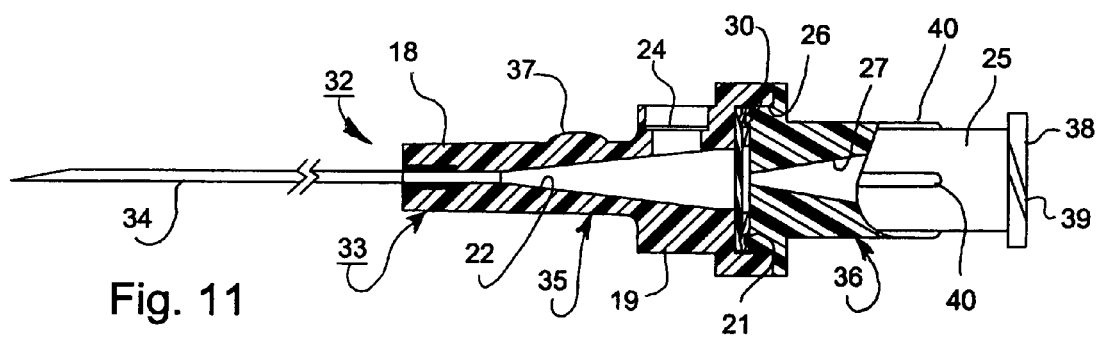

VALVE FOR INTRODUCER NEEDLE

This invention relates to an introducer needle. More particularly, this invention relates to a valve for mounting in one end of an introducer needle.

As is known, various types of devices have been used for infusing liquids into the veins or arteries of a patient and/or for placing devices within the vein or artery of a patient. For example, in one known procedure, use is made of an introducer needle to first gain access to a vein or artery and then a guide wire is slid through the needle into place in the vein or artery. Thereafter, the introducer needle is withdrawn to leave the wire in the patient. Subsequently, a dilator is slid over the guide wire into the vein or artery of the patient in order to dilate the vein or artery, the guide wire is then removed leaving the dilator in place. A catheter is then introduced into the dilator for positioning within the vein or artery. Thereafter, the dilator is removed in a conventional manner while leaving the catheter in place.

Initially, when an introducer needle is first introduced into a patient, there is a need to know when the needle has entered a patient's blood vessel. Generally, the determination is made using a transparent flashback chamber at the proximal end of the introducer needle. When the needle enters the patient's blood vessel, blood will flow through the needle into the flashback chamber. Thus, the clinician is able to see the blood.

U.S. Pat. No. 6,652,490 describes a technique wherein a catheter and introducer needle can be inserted into a blood vessel employing a flashback chamber in the needle. As described, once proper placement has been confirmed, the clinician applies pressure to the blood vessel by pressing down on the patient's skin over the distal tip of the introducer needle and catheter to occlude further blood flow through the introducer needle. Of course, if this step does not occur, the blood would continue to flow out of the introducer needle and onto the clinician and the surrounding area. Thus, a clinician must be attentive and move with dispatch to remove the introducer needle and attach a fluid delivery device, a PRN or a deadener cap to the hub of the catheter.

It is an object of this invention to provide a valve of simple construction that provides a flashback chamber and that prevents a flow of blood out of an introducer needle.

It is another object of the invention to be able to insert a guide wire through an introducer needle into a patient in a bloodless manner.

It is another object of the invention to provide a valve for an introducer needle that can be retrofitted into existing introducer needles.

Briefly, the invention provides a valve for use with an introducer needle that provides a flashback chamber when in use, that prevents an outflow of blood from the introducer needle and that allows a guide wire to be introduced through the introducer needle into a patient in a bloodless seal tight manner.

Typically, the valve is used with an introducer needle that has a hub and a hollow needle secured to and extending from one end of the hub. The valve is mounted in the opposite end of the hub from the hollow needle to prevent a flow of blood out of the hub of the introducer needle.

In accordance with the invention, the valve is constructed of a housing that defines a passage through which a guide wire may pass into the hub of the introducer needle. The housing has a forward end for fitting into the hub of the introducer needle and a rear end for receiving a luer connection. In addition, a seal is disposed within the housing across the passage in order to seal one side of the passage in the forward end of the housing from the other side of the passage in the rear end of the housing. The seal is also provided with a slit to enable passage of a guide wire therethrough while maintaining a circumferential seal on the wire.

The seal is constructed to maintain a seal-tight closure under a pressure of at least 15 pounds per square inch (psi). That is to say, leakage through the slit in the seal will not occur until the pressure in the patient side of the passage exceeds 15 psi.

The housing of the valve is also provided with a port that extends radially of the passage in the forward end of the housing as well as an air filter in the port for passage of air from the valve. The port communicates with the passage in the valve so that any air in the passage may be vented while, at the same time, the filter prevents blood from leaking out of the valve. The filter may be of any conventional type.

When in use, the valve is mounted in the rear end of the hub of the introducer needle prior to insertion of the hollow needle into the vein or artery of a patient. Upon insertion of the hollow needle, blood will fill the hollow needle and the forward end of the passage in the valve and will be blocked from leaking out of the valve by means of the seal in the passage and the seal in the air vent port. Typically, the forward end of the valve housing is transparent so that the passage in the valve acts as a flashback chamber so blood can be viewed by the clinician.

Thereafter, a guide wire may be passed through the seal in the valve and into the introducer needle in a conventional manner by the clinician. During this time, the guide wire passes through the slit in the seal while a seal-tight connection is maintained about the guide wire.

The valve may also be made integral with a hub of an introducer needle rather than being made as a separate device.

These and other objects and advantages of the invention will become more apparent from the following detailed description taken in conjunction with the accompanying drawings, wherein:

FIG. 1 illustrates a side view of an introducer needle of conventional construction;

FIG. 2 illustrates a side view of a valve for mounting in the introducer needle of FIG. 1;

FIG. 3 illustrates a view of the valve of FIG. 2 mounted in the introducer needle of FIG. 1 with a guide wire ready for insertion;

FIG. 4 illustrates a cross-sectional view of the valve of FIG. 2;

FIG. 5 illustrates a front view of the valve of FIG. 4;

FIG. 6 illustrates a rear view of the valve of FIG. 4;

FIG. 7 illustrates an exploded view of the valve of FIG. 4;

FIG. 8 illustrates a front view of the seal employed in the valve of FIG. 4;

FIG. 9 illustrates a front view of a support ring employed in the valve of FIG. 4;

FIG. 10 illustrates a cross-sectional view of the valve of FIG. 4 with a guide wire being inserted; and FIG. 11 illustrates a cross-sectional view of an introducer needle with an integral valve in accordance with the invention.

Referring to FIG. 1, an introducer needle 11 of conventional structure includes a hub 12 and a hollow needle 13 that is secured to and that extends from one end of the hub 12. Typically, the introducer needle 11 is an 18 gauge or 21 gauge needle although other sizes may be used. Also, the needle is typically, 5 to 7 centimeters long although other lengths are possible.

Referring to FIGS. 2 and 4, the valve 14 has a housing 15 that is formed of two pieces 16, 17 that are secured together in permanently fixed co-linear relation and are made of a suitable material, such as a transparent plastic material. The two pieces 16, 17 are secured together, for example, ultra-sonically where the two pieces 16, 17 are made of a suitable plastic or may be adhesively secured together. The forward piece 16 of the housing 15 has a cylindrical nose portion 18 for fitting into a bore (not shown) of the hub 12 of the introducer needle 11, for example, in a slide-fit or friction-fit manner, as indicated in FIG. 3.

Referring to FIGS. 4, 5 and 6, the forward housing piece 16 has a cylindrical section 19 of larger diameter than the nose portion 18 and an annular collar 20 of larger diameter than the cylindrical section 19 that defines an internal recess 21 (FIG. 4).

The forward housing piece 16 also includes a passage 22 that tapers radially inwardly in a direction towards the introducer needle 11, i.e. towards the forward end of the housing 14. This passage 22 communicates with a port 23 that extends radially of the passage 22 within the annular portion 19 and together with the port 23 forms a flashback chamber for receiving blood from a patient's blood vessel when in use. Due to the transparency of the housing piece 16, a clinician can see an accumulation of blood in the flashback chamber.

An air filter 24 of disk shape is disposed within the port 23 to permit the passage of air while preventing the passage of blood therethrough. This air filter is of known construction.

The second or rear piece 17 of the housing 15 has a cylindrical rear portion 25 for receiving a luer connection and a stepped annular collar 26 of larger diameter that fits into the recess 21 of the first housing piece 16. Any suitable means may be used to secure the two pieces 16, 17 together.

In addition, a passage 27 extends through the housing piece 17 that also tapers radially inwardly in a direction towards the introducer needle 11, i.e. in the same direction as the passage 22 tapers.

The valve 14 also has a seal 28 disposed between the two housing pieces 16, 17 and across the respective passages 22, 27 in order to seal the two passages 22, 27 from each other. That is, the seal 28 seals the introducer needle side of the passage through the valve 14 from the opposite side of the passage.

Referring to FIGS. 7 and 8, the seal 28 is in the form of a circular disk having a slit 29 in the center. The nature of the seal 28 is such that the slit 29 will not open until a pressure in excess of 15 psi is exerted thereon.

A support ring 30 of annular shape is also disposed between the seal 28 and the stepped collar 26 of the second housing piece 17. As illustrated in FIG. 9, the support ring 30 has a central aperture larger than the central portion of the seal 28 so as to provide ready access to the slit 29 in the seal 28.

As indicated in FIG. 4, the two housing pieces 16, 17 are secured together in co-linear relation with the seal 28 disposed between the two pieces 16, 17 to block access between the two passages 22, 27.

Referring to FIG. 3, the valve 14 is sized to be slidably mounted in an opposite side of the hub 12 from the hollow needle 13 in a seal tight manner in order to prevent a flow of blood out of the hub 12. Prior to use of the introducer needle 11, the nose portion 18 of the valve 14 is mounted in the rear end of the hub 12. Thereafter, the introducer needle 11 may be introduced into a vein or artery of a patient in the usual manner. At this time, any blood that passes through the hollow needle 13 will pass into the hub 12 and through the passage 22 in the forward end of the valve 14. However, the seal 28 across the passage 22 will block any flow of blood out of the valve 14. At the same time, any air entering into the passage 22 will be vented through the port 23 and the air filter 24. However, blood will be blocked from passing through the air filter 24 because of the nature of the air filter 24.

If necessary, the valve 14 may be removable from the hub 12 of the introducer needle 11 or may remain with the introducer needle 11 for subsequent disposal purposes.

Referring to FIG. 3, a guide wire 31 may be passed through the valve 14 and into the needle 13 of the introducer needle by simply passing the guide wire 31 through the slit 29 in the seal 28, as indicated in FIG. 10. During this time, the seal 28 will maintain a seal-tight fit on the guide wire 31 so that blood does not pass through the slit 29.

The taper of the passage 27 in the rear section 17 of the valve housing 15 serves to guide the guide wire 31 into the slit 29 of the seal 28 while the taper of the passage 22 in the forward section 16 of the valve housing 15 serves to guide the wire 31 into the hollow needle 13 of the introducer needle 11. Thus, the valve 14 also acts as a guide for guiding the guide wire 31 into position for entry into the introducer needle 11.

Referring to FIG. 11 wherein like reference characters indicate like parts as above, the valve construction may be integrally incorporated into the housing of an introducer needle. As illustrated, the integrated construction 32 includes a hub 33 and a hollow needle 34 that is secured to and that extends from one end of the hub 33. In addition, the hub 33 is formed of two hollow tubular pieces 35, 36 that are secured together in co-linear relation and are made of a suitable material, such as a transparent plastic material. These two pieces 35, 36 may be secured together in a similar manner as the pieces 16, 17 of the valve 14.

The forward housing piece 35 has a cylindrical nose portion 18 that receives the hollow needle 34, a cylindrical section 19 of large diameter and a passage 22 that extends throughout and that tapers radially inwardly in a direction towards the hollow needle 34. The passage 22 communicates with a port 23 in the cylindrical section 19 of the housing piece 35 to form a flashback chamber for receiving blood from a patient's blood vessel when in use. As above, an air filter 24 of disk shape is disposed within the port 23.

In addition, an eyespot 37 is formed in the nose portion 18 for viewing any blood in the flashback chamber.

The rear housing piece 36 has a cylindrical portion 25, a stepped annular collar 26 of enlarged diameter at one end that fits into a recess 21 of the forward housing piece 35, a passage 27 that extends through the housing piece 36 and that also tapers radially inwardly in a direction towards the hollow needle 34 and a luer connection 38 with a luer thread 39 at the opposite end.

As above, a seal 28 is disposed between the two housing pieces 35, 36 and across the respective passages 22, 27 in order to seal the two passages 22, 27 from each other. This seal 28 has a slit (not shown) in the center, as above. A support ring 30 of annular shape is also disposed between the seal 28 and the stepped collar 26 of the second housing piece 36.

As illustrated in FIG. 11, the cylindrical rear portion 25 of the rear housing piece 36 has a plurality of circumferentially spaced apart ribs 40 similar to those of the hub 12 of FIG. 1

The structure 32 is used in a similar manner as described above and need not be further described.

The invention thus provides a valve that includes a flashback chamber to detect the presence of blood coming from an introducer needle that has been inserted into a patient, that blocks a flow of blood from the introducer needle into the surrounding environment and that allows a guide wire to be passed into the introducer needle in a bloodless seal tight manner.

The invention also provides a valve of relatively simple construction that can be retrofitted onto existing introducer needles.

Further, the invention provides a valve that may be incorporated into an introducer needle so as to be manufactured therewith without being a separate device.

What is claimed:

1. In combination
   an introducer needle having a hub and a hollow needle secured to and extending from one end of said hub;
   a valve including a forward piece having a transparent nose portion fitting into an opposite end of said hub from said hollow needle, said nose portion having a first tapered passage extending therethrough in communication with said hollow needle and a radially extending port communicating with said passage to form a flashback chamber therewith and a rear piece permanently fixed to said forward piece and having a second tapered passage coaxial with said first tapered passage of said nose portion and tapering radially inwardly in a direction towards said introducer needle for guiding a guide wire therethrough;
   an air filter disposed within said port to permit the passage of air while preventing the passage of blood; and
   a seal disposed between said forward piece and said rear piece within said valve across said passage of said nose portion to seal said first tapered passage from said second tapered passage, said seal having a slit in a center thereof for passage of the guide wire therethrough in circumferentially sealed relation.

2. The combination as set forth in claim 1 wherein said passage of said nose portion tapers radially inwardly in a direction towards said introducer needle.

3. The combination as set forth in claim 1 further comprising a support ring of annular shape between said seal and one of said pieces and having a central aperture.

4. A valve comprising
   a forward piece having a transparent nose portion for fitting into a hub of an introducer needle, said nose portion having a tapered first passage extending therethrough for guiding a guide wire therethrough and a radially extending port communicating with said passage to form a flashback chamber therewith;
   an air filter disposed within said port to permit the passage of air while preventing the passage of blood;
   a rear piece permanently secured to said forward piece and having a second passage tapering radially inwardly in a direction towards said nose portion; and
   a seal disposed between said forward piece and said rear piece and across said first passage to seal said first passage in said nose portion from said second passage in said rear piece, said seal having a slit in a center thereof for passage of the guide wire therethrough in circumferentially sealed relation.

5. A valve as set forth in claim 4 which further comprises a ring abutting said seal peripherally outside said slit and located between said seal and said rear piece.

* * * * *